(12) United States Patent
Greenspan (10) Patent No.: US 8,644,917 B2
(45) Date of Patent: Feb. 4, 2014

(54) CARDIO MAPPING SYSTEM AND METHOD FOR CARDIO MAPPING

(75) Inventor: Allan M. Greenspan, Philadelphia, PA (US)

(73) Assignee: Albert Einstein Healthcare Network, Philadelphia, PA (US)

( * ) Notice: Subject to any disclaimer, the term of this patent is extended or adjusted under 35 U.S.C. 154(b) by 0 days.

(21) Appl. No.: 13/604,168

(22) Filed: Sep. 5, 2012

(65) Prior Publication Data

US 2013/0072774 A1 Mar. 21, 2013

Related U.S. Application Data

(60) Provisional application No. 61/536,730, filed on Sep. 20, 2011.

(51) Int. Cl.
*A61B 5/0452* (2006.01)
(52) U.S. Cl.
USPC ............................ 600/515; 600/374; 600/409
(58) Field of Classification Search
USPC ......................................... 600/374, 409, 515
See application file for complete search history.

(56) References Cited

PUBLICATIONS

Houben, Richard P.M., et al. "Automatic mapping of human atrial fibrillation by template matching." Oct. 10, 2006. Heart Rhythm Society. pp. 1221-1228.*

* cited by examiner

*Primary Examiner* — Christopher D Koharski
*Assistant Examiner* — Michael Carey
(74) *Attorney, Agent, or Firm* — Caesar, Rivise, Bernstein, Cohen & Pokotilow, Ltd.

(57) ABSTRACT

A method and system for determining the mechanism of cardiac arrhythmia in a patient is disclosed. The method basically entails measuring the impedance of cardiac tissue in a portion of the patient's heart using a catheter during an episode of supraventricular tachycardia to produce an iso-impedance map of that cardiac tissue on a video display and analyzing the pattern of the iso-impedance map to differentiate focal arrhythmia caused by a circumscribed region of focal firing and reentrant arrhythmia caused by a macroreentrant circuit. The method can also be used to identify regions of coherent rapidly conducting tissue e.g., Bachman's bundle or the inferoposterior pathway insertion points, to identify focal "mother rotors" throughout the left atrium that may participate in the generation and maintenance of atrial fibrillation and to identify areas of CAFE (complex atrial/fractionated electrograms) that truly reflect these mother rotors.

20 Claims, 6 Drawing Sheets
(5 of 6 Drawing Sheet(s) Filed in Color)

CARDIO MAPPING SYSTEM AND METHOD FOR CARDIO MAPPING

CROSS-REFERENCE TO RELATED APPLICATIONS

This utility application claims the benefit under 35 U.S.C. §119(e) of Provisional Application Ser. No. 61/536,730 filed on Sep. 20, 2011 entitled Cardio Mapping Method, the entire disclosure of that provisional application is incorporated by reference herein.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to electro-anatomic mapping of the heart and more particularly to systems and methods for impedance mapping of endocardial and epicardial surfaces of the heart to identify the mechanism and site of origin of various arrhythmias, and to identify damaged cardiac tissues (scar), as well as coherent, rapidly conducting tissue.

BACKGROUND OF THE INVENTION

Electrical contact mapping of the heart typically involves voltage and activation mapping and is accomplished using a standard multi-polar electrode catheter, e.g., a Biosense Webster deflectable tip mapping/ablation catheter (2 mm or 4 mm tip). The catheter is coupled to a processing unit or analyzer, which in turn is coupled to a video display unit. In use, the catheter is inserted, via the Seldinger technique, in the femoral veins and is positioned under fluoroscopic guidance at predetermined locations in the right atrium, right ventricle, coronary sinus and, if necessary, in the left atrium and left ventricle. The mapping catheter is then translocated to between 50 and 200 different point locations throughout the cardiac chamber of interest during the spontaneously occurring or induced arrhythmia which is either a supraventricular tachycardia (SVT), a ventricular tachycardia (VT) or frequent ventricular premature complexes (VPC's). At each point, with the catheter tip in good contact with the endocardial wall of the chamber of interest, the following electrical parameters are measured and registered by the software in the processing unit to their position in 3-dimensional space on the endocardial surface of the chamber of interest: (1) local electrical activation time (LAT) and (2) tissue voltage (V). That system is also capable of measuring tissue impedance (Z). The measurement of tissue impedance, being for the purpose of differentiating scar tissue from normal tissue or fat from scar tissue, and these measurements are made during normal sinus rhythm.

Figure 2:
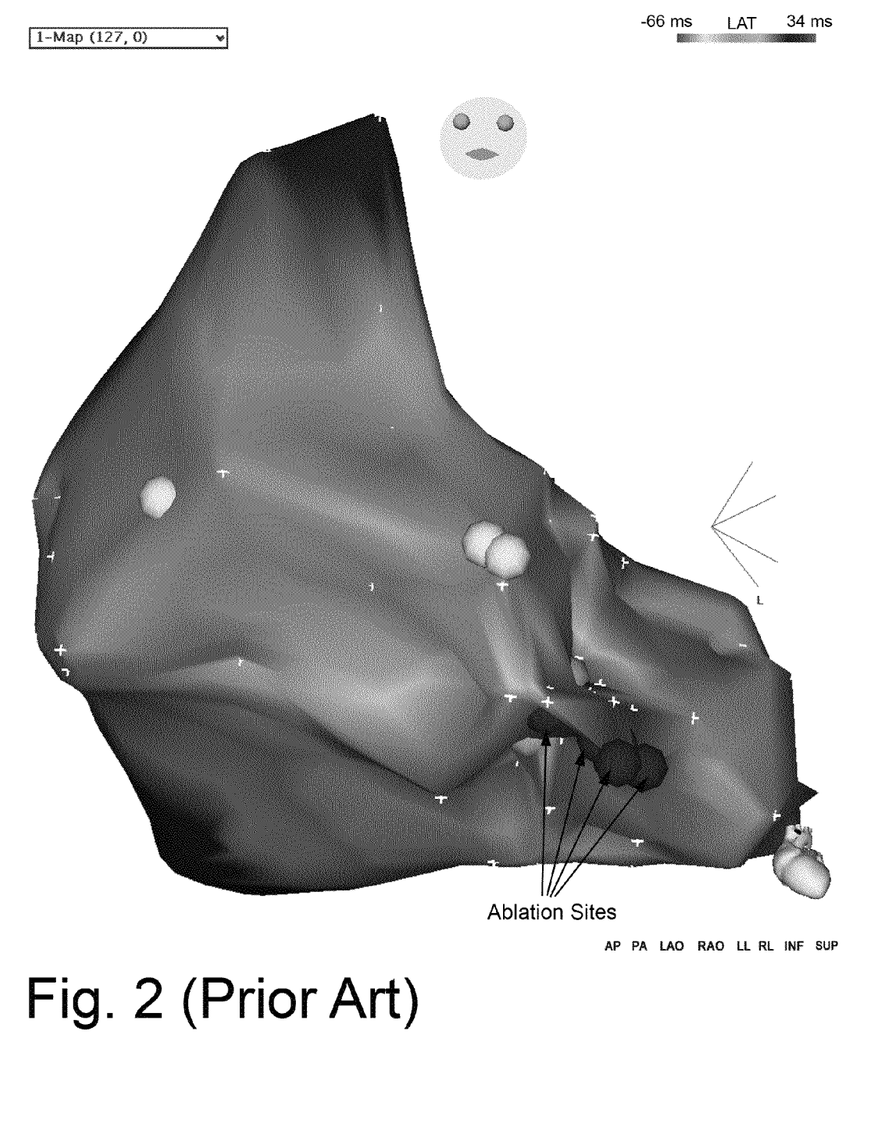
FIG. 2 is an exemplary prior art anterior-posterior view iso-activation map of the right atrium of a patient exhibiting a focal arrhythmia; the successful ablation site correlates with the region of earliest activation as indicated by the red coloration.

An electro-anatomic activation map (such as shown in FIG. 2) is generated for the LAT and tissue voltage and those parameters are displayed on the video display as an iso-activation and an iso-voltage map. The iso-activation map is evaluated for the pattern of activation as either being centripetal or reentrant. A centripetal pattern is one having a focal area of earliest activation with waves of progressively later activation spreading out concentrically from the earliest activation site. This is compatible with a focus of electrical activity firing off rapidly and activating the rest of the chamber sequentially. The other pattern of activation, i.e., reentrant, shows a well defined region where the tissue with the earliest activation time is immediately adjacent to tissue with the latest activation time, indicating that the chamber is being activated sequentially, and continuously as a large reentrant circuit. The iso-activation map demonstrates activation emanating from one region and then sequentially spreading throughout the chamber and finally the returning to the region of earliest activation, as if inscribing a large circle of the spreading electrical wave front.

Heretofore iso-activation maps have typically been color coded so that red indicates early activation sites, blue and purple indicates late activated sites, and orange, yellow and green indicates intermediate activation sites.

Relying on these different patterns of the iso-activation map to differentiate these arrhythmia mechanisms so that appropriate therapy, e.g., ablation, can be applied to the patient can sometimes be misleading and can cause a lot of wasted time and energy in the effort to define the mechanism of the arrhythmia and direct the ablative therapy. The major problem is that a focal arrhythmia can mimic a reentrant arrhythmia, particularly when the focal firing tissue is in another chamber and the electrical wave fronts that travel into the chamber being mapped cause activation in the chamber of interest in a macroreentrant pattern due to anatomic/physiologic barriers that generate one-way conduction in that chamber. Thus, the iso-activation map in the chamber of interest shows the macroreentrant pattern of earliest activated tissue adjacent to latest activated tissue, while the actual arrhythmia generator is a group of cells focally firing elsewhere. Ablating across the presumed reentrant circuit in this scenario to produce a "line of block" to interrupt the reentrant circuit isthmus and terminate the arrhythmia, will have no effect.

There is reason to believe that the above scenario, particularly if it involves the right atrium, is not so infrequent, as in this chamber there are natural anatomic barriers that can confine the conduction of electric current to a fixed pathway, that would mimic a reentrant activation pattern, with a little help from some physiologic barriers that develop when there is associated organic heart disease that cause fibrosis which can lead to anisotropic conduction and physiologic block.

Thus, there presently exists a need for additional methods and systems for identifying/differentiating arrhythmia sources, e.g., discriminating between focal arrhythmias and reentrant arrhythmias. Additionally, there is utility in identifying coherent, rapidly conducting pathways that may be participating in reentrant circuits and to identify damaged cardiac tissues, i.e., scar tissue, that is often the substrate for micro-reentrant circuits. The subject invention addresses those needs.

SUMMARY OF THE INVENTION

One aspect of this invention is a cardiac arrhythmia discrimination system for determining the mechanism of cardiac arrhythmia in a patient. The cardiac arrhythmia discrimination system comprises a catheter and an associated processing unit. The catheter and the processing unit are arranged to measure the impedance of cardiac tissue of the patient at various selected points on the endocardial/epicardial surface of the patient's heart during a spontaneously occurring or induced arrhythmia, e.g., supraventricular tachycardia, and providing the geometric position of each of the points on the patient's heart. Each of the impedance measurements and point positions are recorded by the system. The system is arranged to determine if a point on the patient's heart exhibits low impedance ($Z_{low}$), wherein $Z_{low} \leq Z_{min}+0.1(Z_{max}-Z_{min})$, where $Z_{min}$ is the minimum impedance measured and $Z_{max}$ is the maximum impedance measured.

The system is also arranged to discard from its impedance measurements any points associated with tissue voltage of less than 0.5 mV indicating poor contact of the catheter to the cardiac tissue, as well as any points that are too internal to the anatomic shell (e.g., >1 mm internal to a 15 degree spherical arc of curvature with a radius of 1.5-2 cm inscribed by a local group of measured points on the heart chamber shell) or points with far-field low amplitude electrograms, and evaluates the remaining points of measured impedance to determine if there is an area of approximately $3.4\pm2$ cm$^2$ or $2.4\pm1.8\%$ of the atrial surface area having plural $Z_{low}$ points therein.

In accordance with another aspect of this invention the system includes a video display coupled to the processing unit and which is arranged to produce an iso-impedance map of the cardiac tissue. The iso-impedance map is colored to represent differing impedances measured by the catheter to enable a user of the system to visually analyze the color pattern of the iso-impedance map to differentiate a focal arrhythmia caused by a group of cells focally firing, from a reentrant arrhythmia caused by a macroreentrant circuit.

In accordance with another aspect of this invention there is provided a method determining the mechanism of cardiac arrhythmia in a patient. The method entails measuring impedance of cardiac tissue of the patient at various selected points on the patient's heart using a catheter during spontaneously occurring or induced arrhythmia. Measurements of impedances at points associated with tissue voltage of less than 0.5 mV or poor contact of the catheter to the cardiac tissue are discarded as are impedance measurements from mapping points that are too internal to the anatomic shell or points with far-field low amplitude electrograms. The remaining points of measured impedance are evaluated to determine if there is an area of approximately $3.4\pm2$ cm$^2$ or $2.4\pm1.8\%$ of the atrial surface area having plural low impedance ($Z_{low}$) points therein, where $Z_{low} \leq Z_{min}+0.1(Z_{max}-Z_{min})$ and where $Z_{min}$ is the minimum impedance measured and $Z_{max}$ is the maximum impedance measured, wherein the existence of said area of said plural low impedance ($Z_{low}$) points therein indicates a focal arrhythmia caused by a circumscribed region of focal firing and wherein the absence of said area of said plural low impedance ($Z_{low}$) points therein indicates a reentrant arrhythmia caused by a macroreentrant circuit.

The measurements may be displayed in the form of an iso-impedance map, which may appear on a video display to facilitate appropriate therapy, e.g., ablation.

DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
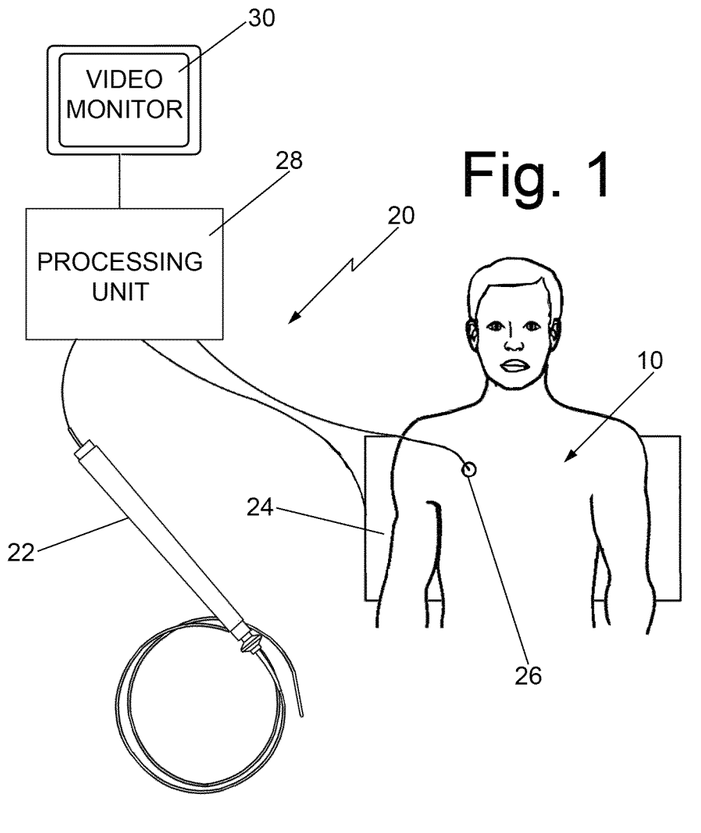
FIG. 1 is an illustration including a block diagram of one exemplary system for measuring the impedance of cardiac tissue and providing an iso-impedance map thereof to enable the user of the system to determine if the patient's arrhythmia is the result of reentrant activation or focal activation.

Referring now to the various figures of the drawing wherein like reference characters refer to like parts, there is shown in FIG. 1 a cardiac arrhythmia discrimination system 20 for determining the mechanism of cardiac arrhythmia in a patient. The details of the system 20 will be described later. Suffice it for now to state that in accordance with one aspect of this invention the system 20 and its method of use effects electro-anatomic mapping of cardiac arrhythmias to help differentiate the two most common mechanisms of these arrhythmias, i.e., focal firing based arrhythmias versus macroreentrant based arrhythmias. To that end the system and method of this invention employs a catheter and associated circuitry to effect the measurement of cardiac tissue impedance during an arrhythmia (either spontaneously occurring or induced) and to produce an iso-impedance map of the cardiac tissue to enable the user of the system to determine if there is a contiguous area of low impedance, e.g., an area of approximately 1.4-5.4 cm$^2$ representing 0.6-4.2% of the surface area of the chamber of interest which would reflect a group of some 400,000-600,000 cardiac myocytes being depolarized synchronously by after-depolarizations, that is driving activation of the cardiac chamber. This contiguous low impedance area, hereinafter referred to as a "CLIA", results from the opening of a multitude of "stretch activated" channels in addition to the normal membrane channels responsible for the normal cardiac action potential, in these focal arrhythmias. This is in contrast to the macroreentrant arrhythmias, where a single focal firing triggers off a reentrant circuit where all the tissue is activated by the sequential opening of the standard membrane channels. These two mechanisms can be differentiated by the presence (focal firing) or absence (macroreentry) of a CLIA during the arrhythmia.

While the exemplary embodiment of the system and method of this invention entails the production of an iso-impedance map to indicate the particular mechanism causing the arrhythmia, other systems and method are contemplated by this invention to enable such discrimination. Thus, for example, the system 20 may be designed to merely produce a perceptible signal, e.g., visible or audible or both, indicating the presence of a CLIA, instead of producing an iso-impedance map.

The successful identification of a CLIA requires that the cardiac tissue impedance measurements are all due to accurate measurement of normal myocardial cell impedance and are not artifactually low due to a number of causes. Such artifactually low impedance readings include measurement of scar areas (exhibited by low voltage and low impedance) or measurements involving inadequate tissue contact by the measuring instrument, e.g., the particular point measured may be too internal and therefore the catheter's measuring tip may not have been in sufficient contact with the endocardial tissue surface to get a true impedance measurement. Measurements of impedance values from fibrous tissue, such as the fibrous valve rings, are also expected to exhibit low impedance. Also, as will be described later, the definition of low impedance is based on the range of tissue impedances measured during the arrhythmia in the chamber of interest. Thus, artifactually high impedances need to be discarded from the measurements made in the interest of accuracy. Examples of artifactually high impedances are those measured in the great veins and the coronary sinus, where the smaller contribution of blood pool shunt impedance increases the measured impedance.

Various contact electrical mapping catheter systems are commercially available and can be used, with or without modification (as explained below), for carrying out the methodology of this invention. One such system is the NOGA® XP System that is available from Biosense Webster. That system utilizes a location detection technology, i.e., magnetic sensor navigation, and is shown in FIG. 1. That system 20 includes a deflectable tip, multi-polar, mapping/ablation catheter 22 having a 2 mm or 4 mm tip, an associated magnetic field-generating location pad 24, an external location reference patch 26 and an electronic processing unit 28. The catheter 22 includes a miniature passive magnetic field sensor. The location sensors determine the location and orientation of the mapping catheter in six degrees of freedom (DOF) by sensing changes in the magnetic field produced by the pad 24. The system's electronics are arranged to record and process activation time, tissue impedance, tissue voltage and the position of the recording in three dimensional space relative to the electro-anatomic shell to provide the user with the electrical parameters measured at each of the contact point in chamber of interest.

In accordance with one aspect of this invention the system includes a video display or monitor 30. The monitor serves to provide a graphic visual display in the form of an iso-impedance map of the chamber of interest and can also display the various measured parameters and the location data for the impedance and voltage measurements acquired by the catheter 22. The iso-impedance map comprises a 3D color-coded reconstructed representation of the heart. The color-coding enables quick visualization of the measured impedance of the mapped tissue, in correlation with its anatomical location and is presented in real-time. The processing unit 28 includes software which takes the readings acquired by the catheter 22 to provide the map. Some exemplary color coded maps are shown in FIGS. 3, 4A, 4B and 5.

In order to ensure that only readings which are indicative of true cardiac impedance are considered by the system, those impedance readings representing artifactually low or artifactually high impedance measurements are discarded and the remaining valid impedance points kept and analyzed. To that end, the processing unit may include software/firmware to automate the data acquisition and processing (e.g., the discarding of artifactually low and/or artifactually high impedance measurements) to produce the iso-impedance map. If the system doesn't include such software/firmware the user of the system will decide whether or not to use or discard measured impedance points. Thus, depending upon the construction of the system 20, either the user of the system or the software/firmware in the system evaluates the impedance measurements made by the system and discards those impedance measurements for any points associated with a "low" tissue voltage (e.g., less than 0.5 mV). So too, any points representative of a far-field electrogram configuration (i.e., low dV/dt) or prolonged duration or with highly fractionated electrograms are discarded. Tissue impedance at too great a distance internal to the calculated radius of the arc of the electroanatomic shell (i.e., >1 mm internal to a 15 degree spherical arc of curvature with an atrial shell diameter of 4 cm and a wall thickness of 1.5-2.0 mm as processed by the data processor) are also be discarded as likely representing low impedance due to poor contact.

It is noted that pressure sensing ablation catheters are becoming available. Such catheters may be incorporated into the system of this invention to enable the user (or the system itself) to quantify the contact made by the catheter to the cardiac tissue to thereby provide a more accurate way of identifying low impedance measurements resulting from poor contact. Other means may also be provided in the system to quantify or determine if good catheter contact is made to provide an accurate measurement of tissue impedance at the contact point.

In any case, of those impedance measurement points that are kept, the system determines if each retained point exhibits low impedance ("$Z_{low}$"), wherein $Z_{low} \leq Z_{min} + 0.1(Z_{max} - Z_{min})$, where $Z_{min}$ is the minimum impedance measured and $Z_{max}$ is the maximum impedance measured. In addition the system determines the normal impedance ("$Z_{normal}$") of the patient's cardiac tissue, wherein $Z_{normal} \geq Z_{min} 0.2(Z_{max} - Z_{min})$. Those retained point are then used by the system to produce an iso-impedance map, such as those shown in FIGS. 3 and 4A,4B and 5, wherein the differing impedance measurements are color coded to the anatomy of the heart and the map displayed on the video monitor 30.

In the exemplary maps shown in FIGS. 3 and 4A,4B and 5 low impedance points of the cardiac tissue are shown by red, whereas normal impedance points are shown by purple, with intermediate impedance points between red and purple ranging from yellow to green to blue. In accordance with one aspect of this invention the resulting impedance map is evaluated by the user to determine if there is an area of approximately 3.4±2 cm$^2$ or 2.4±1.8% of the atrial surface area having plural $Z_{low}$ points therein. Such a contiguous low impedance area (i.e., a CLIA) indicates a focal arrhythmia caused by a circumscribed region of focal firing, whereas the absence of a CLIA indicates reentrant arrhythmia caused by a macroreentrant circuit.

The maps of FIGS. 3, 4A, 4B and 5 represent respective impedance maps of a portion of the heart of patients that have been produced using the system and method of this invention by measuring the impedance of the cardiac tissue during an SVT episode (either naturally occurring or induced). Such maps can be used to characterize electrical activation patterns of the chamber of interest and help to differentiate a macroreentrant activation pattern (uniform distribution of tissue impedances that are >minimum impedance plus 20% of the difference between minimum and maximum tissue impedance) from a centripetal activation pattern indicative of a focal site of origin. Areas of concentrated low impedance can also identify regions of tissue where there is rapid coherent conduction of electrical currents due to specialized conducting bundles, e.g., Bachman's bundle, or the infero-posterior intra-atrial pathway.

Figure 3:
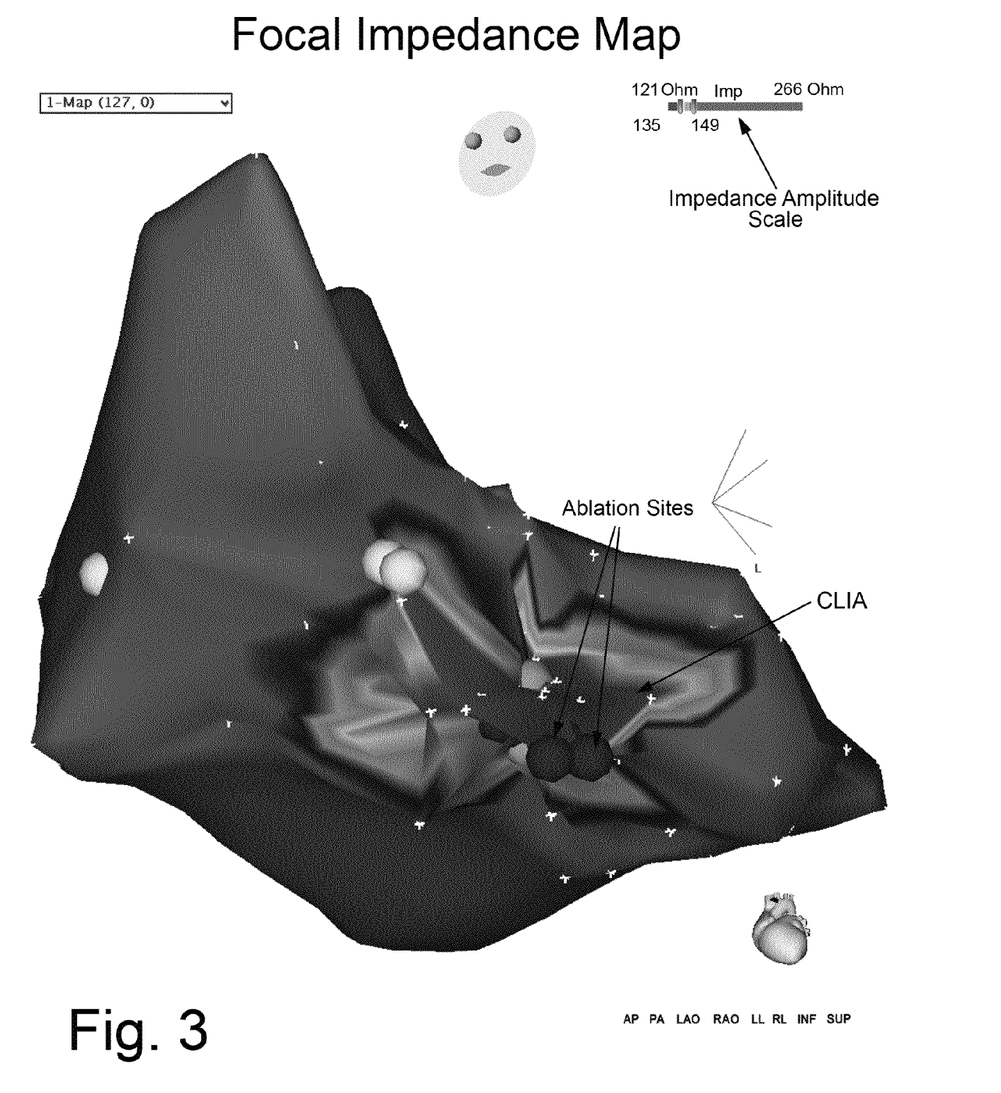
FIG. 3 is an exemplary iso-impedance map of the patient of FIG. 2, with the iso-impedance map of the right atrium being in a shallow left anterior oblique projection slightly different from the view of FIG. 2, but produced using the method and system of this invention and showing a focal activation pattern as evidenced by the contiguous low impedance area or CLIA.

FIG. 3 is an iso-impedance map showing a patient ("Patient A") undergoing an arrhythmia resulting from a focal firing mechanism. As can be seen therein, a focal area of low impedance (CLIA), indicating a focal firing mechanism, is denoted by a contiguous low impedance area of 1.4-5.8 cm$^2$ (the red-yellow area) located infero-septally adjacent to the tricuspid annulus. If the areas of minimum impedance have a much smaller surface area, i.e., <1.0 sq. cm, they are not considered to represent the critical mass of cells required for focal firing to generate large enough local circuit currents to depolarize the rest of the cardiac chamber. The ablation points for the treatment of this patient's condition are shown by the small circular red areas designated "ablation sites". A comparable view iso-activation map (LAT map) of Patient A produced in accordance with the prior art is shown in FIG. 2.

Figure 4A:
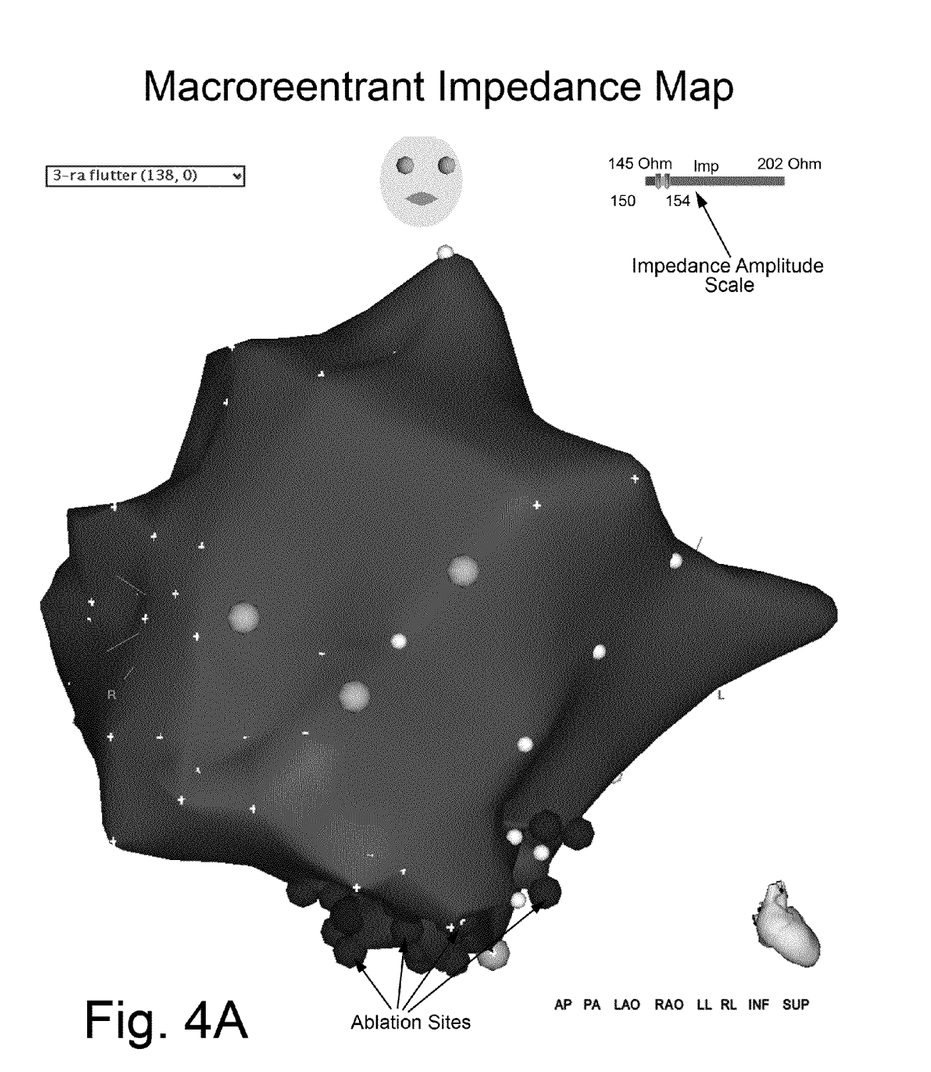
FIG. 4A is an exemplary right anterior oblique iso-impedance map of the right atrium of another patient produced using the method and system of this invention and showing the patient undergoing a macroreentrant based arrhythmia, i.e., isthmus dependent atrial flutter; as evidenced by the uniform impedance pattern with no CLIA.
Figure 4B:
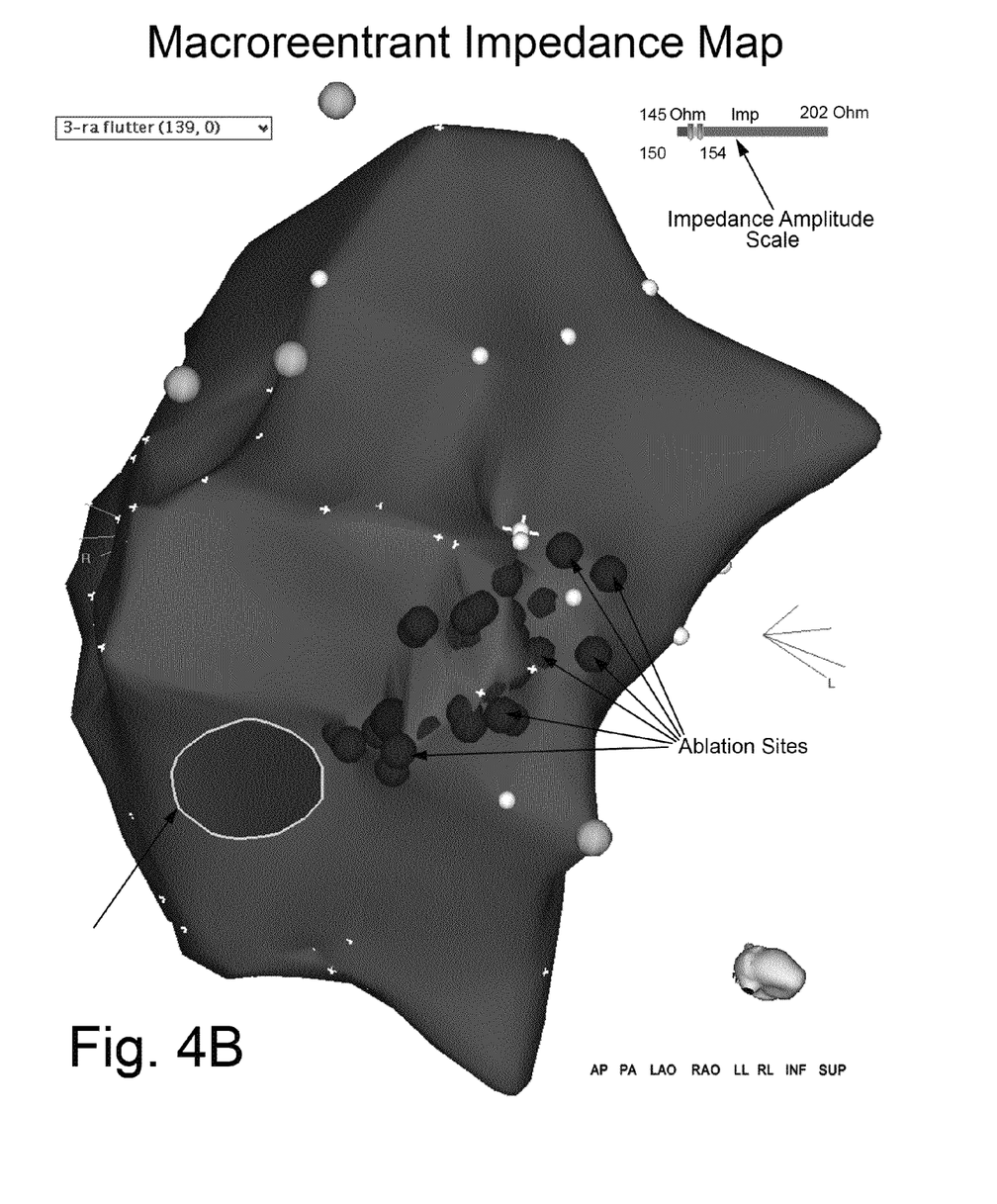
FIG. 4B is another exemplary iso-impedance map of the right atrium of the patient of FIG. 4A, with this view being a left anterior oblique caudal view showing a macroreentrant impedance map pattern, i.e., uniform impedance with no CLIA.
Figure 5:
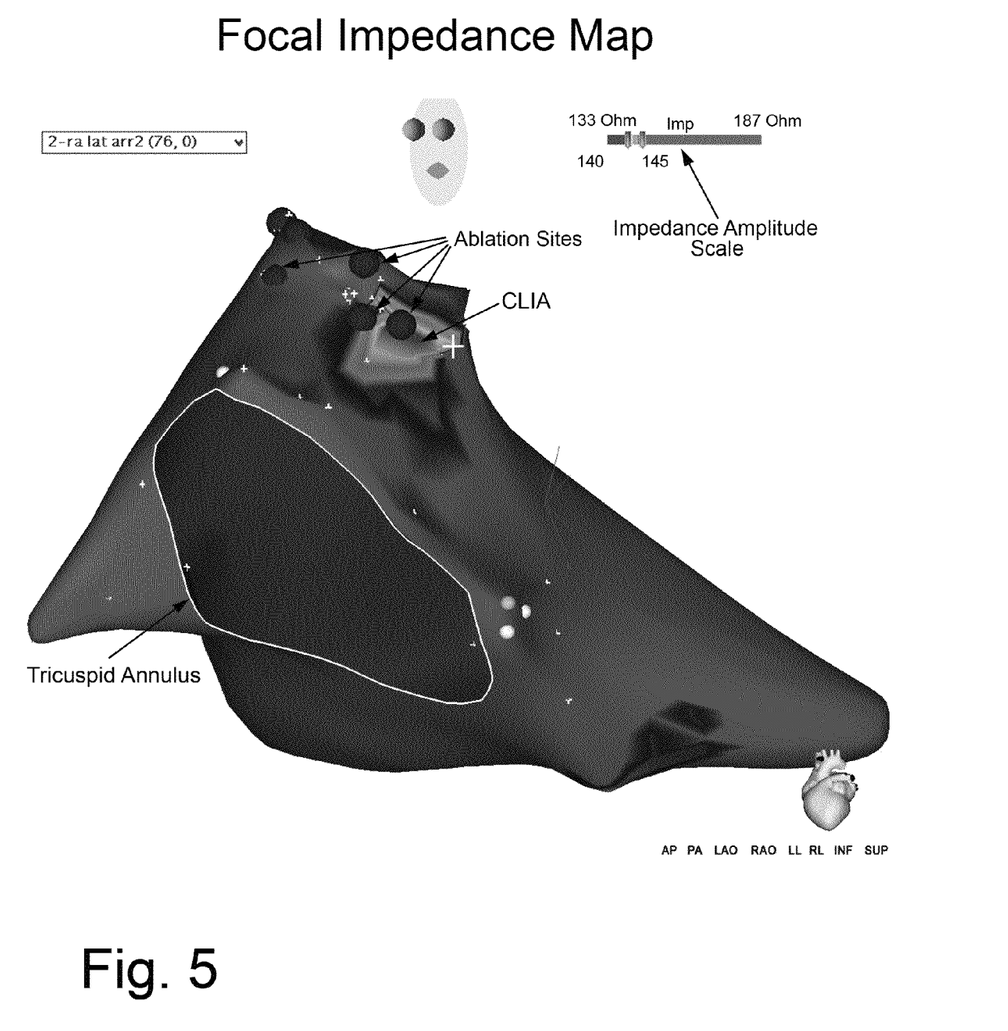
FIG. 5 is an exemplary left anterior oblique view iso-impedance map of the right atrium in the patient of FIGS. 4A and 4B produced using the method and system of this invention during an induced focal atrial tachycardia that occurred the same day and showing a contiguous low impedance area superior-laterally indicative of the focal-based arrhythmia.

Turning now to FIG. 5 there are shown an iso-impedance map of another patient ("Patient B") undergoing an arrhythmia. This map reveals that the mechanism causing Patient B's arrhythmia is most compatible with a focal firing mechanism since the iso-impedance map shows a focal area of low impedance (CLIA) supero-laterally in the right atrium. With this knowledge appropriate therapy, e.g., radiofrequency ablation, was carried out by directing radiofrequency energy from the catheter 22 to the desired ablation points (not shown in FIG. 5) on Patient B's heart. After the ablation procedure had been accomplished the arrhythmia was attempted to be re-induced in Patient B in order to check the effectiveness of the ablation procedure. In this case, it was possible to induce another arrhythmia in Patient B since Patient B was determined to also have a macroreentrant based arrhythmia. In particular, FIGS. 4A and 4B are iso-impedance map of Patient B taken shortly after the ablation procedure for remediating Patient B's focal based arrhythmia. As can be seen in FIGS. 4A and 4B the iso-impedance maps are generally uniform and there are is no focal area of low impedance (CLIA), thereby indicating that the mechanism causing Patient B's other arrhythmia was most compatible with macroreentry. With this knowledge additional ablation was performed on Patient B by directing radiofrequency energy from the catheter to the critical isthmus necessary to interrupt the reentrant circuit. After that ablation procedure programmed atrial stimulation was performed to determine if any arrhythmias were still inducible in Patient B, and none were, thereby indicating that the two ablation procedures had been successful. The ablation points for Patient B are show by the red circles in the maps of FIGS. 4A, 4B and 5.

As should be appreciated by those skilled in the art, since Patient B exhibited two different types of arrhythmias on the same day which are reflected in the different maps of FIGS. 4A, 4B and 5, it is unlikely that Patient B's impedance map patterns are the result of some structural abnormality, e.g., fibrosis, rather than the physiologic characteristics of the two arrhythmias as the heart's structure will not have changed during the period of time between the two arrhythmias.

It should be noted that the theory on which the methodology of this invention is based is as follows: it is known that areas of focal firing involve cells that develop triggered automaticity and the usual mechanism results from the development of "after depolarizations". This physiologic mechanism is based on increased intracellular $Ca^{+2}$ fluxes that cause an increased intracellular $Ca^{+2}$ concentration that persists throughout the cardiac cycle, and that generates delayed (with respect to the duration of the normal action potential) depolarizing inward currents via the Na/Ca exchanger and via stretch activated cationic channels. Experimental and computer modeling data suggests that to generate enough local circuit current to overcome source-sink buffering effects of the syncytial nature of atrial tissue, and produce regenerative depolarizing wave fronts, that would activate a whole cardiac chamber, would take a volume of some 500,000-700,000 cardiac muscle cells, that would all be firing off simultaneously but out of synch with the normal activation of the cardiac chamber, to generate the focal arrhythmia. Because these additional channels are open, causing additional transmembrane currents to flow, the tissue impedance measured in this region should be appreciably lower than the rest of the cardiac chamber being activated by the normal channels that open to generate the standard cardiac action potential. Whereas in an SVT due to a macroreentrant circuit activation, the cardiac chamber of interest, after an initiating out of sync, early depolarization from an errant group of cells with isolated non-repetitive focal firing, the recurrent activation of the cardiac chamber of interest proceeds via the transmission of local circuit currents and sequential activation of the chamber via the normal action potential dependent membrane channels. Thus, the pattern of tissue impedance is relatively uniform and normal, with no focal region of lower tissue impedance relative to the average, as clearly shown in the map of FIGS. 4A and 4B.

Indeed in one preliminary observation, in a group of patients with long RP supraventricular tachycardia, which can be due to either a focal firing mechanism e.g., focal atrial tachycardia (AT) or a macroreentrant mechanism e.g., atrial flutter (AFl), these two different iso-impedance map patterns are observed. For example, a focal AT exists if there is a focal contiguous area of 1.4-5.8 cm$^2$ of low impedance, i.e., ≤the minimum chamber impedance plus 10% of the difference between minimum and maximum chamber impedances, whereas a macroreentrant mechanism exhibits no such focal area. The proof that these two different patterns of the iso-impedance maps do reflect these two different mechanisms is that the ablation procedures deployed to terminate these arrhythmias, based on the mechanisms defined by these different iso-impedance map patterns, are almost uniformly successful. Further still, in the case of the focal low impedance map pattern, not only does this identify the mechanism as being due to a site of focal firing, but it also localizes the region of focal firing, as the successful ablation site is usually contained in the CLIA or within, 10-25 mm of the center of the CLIA.

Some preliminary impedance measurements in patients with SVT following implantable cardioverter defibrillator (ICD) insertion, which turns out to be due to either atrial flutter (a macroreentrant arrhythmia) or a focal atrial tachycardia (rapid focal firing of a group of atrial cells) have been made, in approximately 50 patients. These preliminary impedance maps seem to support the theory that the two arrhythmia mechanisms can be readily differentiated by the differences in the iso-impedance maps. The focal atrial tachycardias show a concentrated contiguous area of relatively low impedance defined as ≤minimum impedance plus 10% of the difference between the minimum and maximum impedance. Furthermore, the area of low impedance seems to be approximately 1.4-5.8 cm$^2$. The literature suggests that a focal atrial tachycardia that results from calcium action potentials due to "after depolarizations" would require 700,000 atrial cells synchronously firing to activate the entire atrium. Using data from the ultrastructure literature, the surface area of a single atrial cell is approximately $1.9 \times 10^{-6}$ cm$^2$. Thus the surface area of a group of 700,000 atrial cells causing a focal atrial tachycardia would be 1.33 $cm^2$, which is in the range of the measurements of the focal low impedance area found on the iso-impedance maps produced in accordance with this invention.

It is contemplated that in further refining the impedance mapping technique of this invention by using smaller surface area electrode catheters, that reduce the contribution of the blood pool shunt impedance which decreases the composite measured impedance, one can more accurately measure the actual tissue impedance, and may see a reduction in the contiguous low impedance surface area more commensurate with that predicted by atrial cell anatomic calculations, i.e., 1.33 $cm^2$.

The iso-impedance maps are displayed in an analogous fashion to voltage amplitude maps. This is accomplished, for example, by setting a hypothetical range of low impedance at less than or equal to the minimum tissue impedance measured+10% of the difference between the minimum and maximum measured impedances with the color scheme of red; intermediate impedances as between the minimum+10%×(maximum−minimum impedances) and the minimum+20%×(maximum−minimum impedance) denoted by a color transition from orange to yellow to green to blue, and normal impedance as minimum impedance+20%×(maximum−minimum impedance) denoted by purple. Similarly, iso-voltage maps set minimum tissue voltage as <0.5 mV denoted by red, normal voltage as >1.5 mV denoted by purple, and intermediate voltages as 0.5-1.5 mV denoted by the transition of colors from orange to yellow to green to blue. It should be noted that the particular colors chosen are arbitrary and other color schemes can be used for the various impedances or voltages displayed in the maps.

As will be appreciated by those skilled in the art, and as discussed above, the existing technique of LAT mapping (such as shown in FIG. 2) can yield confusing results. For example, a focal atrial tachycardia emanating from the intraatrial septum or from the left atrium can cross the atrial septum and activate the right atrium preferentially in a unidirectional fashion because of differences in refractoriness and conduction times through the various atrial conduction bundles, thereby mimicking a macroreentrant circuit pattern when the actual arrhythmia mechanism is focal. In contradistinction, an iso-impedance map produced using the methodology of this invention is not subject to such confusion, as a focal arrhythmia source generates focal contiguous areas of low impedance, i.e., a CLIA and not a uniform, normal impedance map. Thus, the methodology of subject invention enables one to differentiate an arrhythmia due to a macroreentrant circuit from one due to a circumscribed region of focal firing. In this regard, it is believed that focal arrhythmias demonstrate a contiguous low impedance area (CLIA) due to opening of stretch activated channels and activation of the Na/Ca exchanger associated with after-depolarizations, from a confined area that cause focal firing. This can be contrasted to the more uniform distribution of impedance believed to be likely observed with macroreentrant arrhythmias due to the transmission of normal action potentials which result from the sequential opening of the standard ionic membrane channels. In particular, focal atrial tachycardia impedance maps consistently show a typical pattern of an isolated contiguous low impedance area (CLIA) of 3.4±2.0 cm representing 2.4+1.8% of the total atrial surface area. Macroreentrant SVT impedance maps show no such CLIAs and have a more uniform impedance pattern. Thus, the contiguous low impedance area in focal atrial tachycardia impedance maps can help localize the region where RF ablation lesions should be concentrated. It can also identify regions of coherent rapidly conducting tissue, e.g., Bachman's bundle, or the inferoposterior pathway insertion points. In addition, it is believed, that the subject methodology may be able to identify focal "mother" rotors throughout the left atrium that may participate in the generation and maintenance of atrial fibrillation and may be able to identify areas of CAFE (complex atrial fractionated electrograms) thought to reflect these "mother" rotors better than analog electrical recordings currently in use. A still further advantage of the subject invention is that since current usage of conventional contact mapping systems focuses on voltage and activation mapping, differentiation of macroreentrant circuits from focal arrhythmias requires measurement of parameters at a large number of sites throughout the chamber of interest, e.g., 75-150 points. In contradistinction, the impedance mapping methodology of this invention may produce a viable map with fewer points, e.g., approximately 30-50, thereby reducing the time for the mapping procedure.

As should be appreciated from the foregoing by those skilled in the art the system and methods of this invention enable one to readily discriminate a focal arrhythmia from reentrant arrhythmia by virtue of the existence or absence of a CLIA. To that end, the system is arranged to measure and register plural valid impedance measurements to the anatomy of the cardiac chamber of interest, with either the user of the system or software/firmware in the system discarding artificially inaccurate impedance measurements to provide the valid impedance measurements. The system then analyzes the retained impedance measurements to determine if a CLIA exists and the results of the analysis can be provided as an iso-impedance map and/or a perceptible signal to indicate the presence of a CLIA. In addition, the system and method of this invention can also be used to identify regions of coherent rapidly conducting tissue e.g., Bachman's bundle or the inferoposterior pathway insertion points, to identify focal "mother rotors" throughout the left atrium that may participate in the generation and maintenance of atrial fibrillation and to identify areas of CAFE (complex atrial/fractionated electrograms) that truly reflect these mother rotors.

A further possible refinement of the subject invention may allow the identification of actual reentrant pathway critical isthmuses and their localization with high density impedance mapping. A high density multipolar mapping catheter, which is currently in development, should allow greater resolution in identifying regions of rapid coherent conduction (low impedance pathway) surrounded by areas of anisotropic conduction which forms regions of high impedance corridors due to functional conduction block. This could help direct ablation to such low impedance conductions pathways that form the critical isthmus of the reentrant pathway. In atypical right atrial flutters and most left atrial flutters, LAT maps and entrainment mapping fail to reliably identify and localize these critical isthmuses.

Without further elaboration the foregoing will so fully illustrate my invention that others may, by applying current or future knowledge, adopt the same for use under various conditions of service.

I claim:

1. A cardiac arrhythmia discrimination system for determining the mechanism of cardiac arrhythmia in a patient, said cardiac arrhythmia discrimination system comprising, a catheter and an associated processing unit, said catheter and said processing unit being arranged to measure the impedance of cardiac tissue of the patient at various selected points on the patient's heart during a spontaneously occurring or induced arrhythmia and providing the geometric position of each of said points on the patient's heart, and wherein each of said measurements and positions are recorded by said system, said system being arranged to determine if a point on the patient's heart exhibits low impedance ($Z_{low}$), wherein $Z_{low} \leq Z_{min} + 0.1(Z_{max} - Z_{min})$, where $Z_{min}$ is the minimum impedance measured and $Z_{max}$ is the maximum impedance measured, said system being arranged to discard from its impedance measurements any points associated with tissue voltage of less than 0.5 mV or poor contact of the catheter to the cardiac tissue and impedance measurements from mapping points that are too internal to the anatomic shell or points with far-field low amplitude electrograms, and evaluating the remaining points of measured impedance to determine if there is an area of approximately 3.4±2 cm² or 2.4±1.8% of the atrial surface area having plural $Z_{low}$ points therein.

2. The cardiac arrhythmia discrimination system of claim 1 wherein said system is arranged to determine the normal impedance ($Z_{normal}$) of the patient's cardiac tissue, wherein $Z_{normal} \geq Z_{min} + 0.2(Z_{max} - Z_{min})$.

3. The cardiac arrhythmia discrimination system of claim 1 wherein said points that are too internal to the anatomic shell are >1 mm internal to a 15 degree spherical arc of curvature with a radius of 1.5-2 cm inscribed by a local group of measured points on the heart chamber shell.

4. The cardiac arrhythmia discrimination system of claim 1 wherein said system is arranged to produce a perceptible signal upon the detection of said plural $Z_{low}$ points within said area.

5. The cardiac arrhythmia discrimination system of claim 1 wherein said processing unit including magnetic sensor navigation to provide the geometric position of each of said points on the patient's heart.

6. The cardiac arrhythmia discrimination system of claim 2 wherein said system additionally comprises a video display coupled to said processing unit and being arranged to produce a iso-impedance map of the cardiac tissue, said iso-impedance map being colored to represent differing impedances measured by said catheter to enable a user of said cardiac arrhythmia discrimination system to visually analyze the color pattern of said iso-impedance map to differentiate a focal arrhythmia caused by a circumscribed region of focal firing from reentrant arrhythmia caused by a macroreentrant circuit.

7. The cardiac arrhythmia discrimination system of claim 1 wherein said catheter is arranged to determine the amount of pressure applied by it onto the cardiac tissue to thereby enable the system to determine if the catheter has made good contact with the cardiac tissue.

8. The cardiac arrhythmia discrimination system of claim 1 wherein said catheter comprises a multipolar electrode catheter.

9. The cardiac arrhythmia discrimination system of claim 8 wherein said catheter is a radiofrequency ablation catheter.

10. The cardiac arrhythmia discrimination system of claim 6 wherein $Z_{low}$ is represented by the color red in said iso-impedance map and wherein $Z_{normal}$ is represented by the color purple in said iso-impedance map, with intermediate impedances being represented by different colors.

11. A method of determining the mechanism of cardiac arrhythmia in a patient comprising:

a) measuring impedance of cardiac tissue of the patient at various selected points on the patient's heart using a catheter during a spontaneously occurring or induced arrhythmia;
b) recording each of said measurements the geometric position of each of said points on the patient's heart;
c) discarding from said impedance measurements any points associated with tissue voltage of less than 0.5 mV or poor contact of the catheter to the cardiac tissue and impedance measurements from mapping points that are too internal to the anatomic shell or points with far-field low amplitude electrograms; and
d) evaluating the remaining points of measured impedance to determine if there is an area of approximately 3.4±2 cm² or 2.4±1.8% of the atrial surface area having plural low impedance ($Z_{low}$) points therein, where $Z_{low} \leq Z_{min} + 0.1(Z_{max} - Z_{min})$ and where $Z_{min}$ is the minimum impedance measured and $Z_{max}$ is the maximum impedance measured, wherein the existence of said area of said plural low impedance ($Z_{low}$) points therein indicates a focal arrhythmia caused by a circumscribed region of focal firing and wherein the absence of said area of said plural low impedance ($Z_{low}$) points therein indicates a reentrant arrhythmia caused by a macroreentrant circuit.

12. The method of claim 11 wherein said points that are too internal to the anatomic shell are >1 mm internal to a 15 degree spherical arc of curvature with a radius of 1.5-2 cm inscribed by a local group of measured points on the heart chamber shell.

13. The method of claim 11 wherein said method additionally comprises providing an iso-impedance map of the cardiac tissue from said measurement, said iso-impedance map being colored to represent differing impedances measured to enable a person to visually analyze the color pattern of said iso-impedance map to differentiate a focal arrhythmia caused by a circumscribed region of focal firing from reentrant arrhythmia caused by a macroreentrant circuit.

14. The method of claim 11 wherein said catheter is a multipolar electrode catheter which is inserted into a chamber or coronary sinus in the patient's heart with direct contact with the adjacent the cardiac tissue.

15. The method of claim 11 wherein said method is carried out during an episode of supraventricular tachycardia in the patient.

16. The method of claim 11 additionally comprising ablating appropriate cardiac tissue resulting from the evaluation of the measurements.

17. The method of claim 13 additionally comprising ablating appropriate cardiac tissue resulting from the evaluation of the iso-impedance map.

18. The method of claim 11 additionally comprising utilizing magnetic sensor navigation to provide the geometric position of each of said points on the patient's heart.

19. The method of claim 15 comprising providing said iso-impedance map on a video display.

20. The method of claim 11 being applied in conjunction with high density impedance mapping utilizing a multipolar mapping catheter to define critical isthmuses surrounded by regions of anatomic or physiologic conduction block in left atrial and atypical right atrial flutters that can then be targeted by radiofrequency ablation.

* * * * *